(12) United States Patent
Wolff et al.

(10) Patent No.: US 8,865,195 B2
(45) Date of Patent: *Oct. 21, 2014

(54) FOAMING FORMULATIONS AND CLEANSING PRODUCTS INCLUDING SILICONE POLYESTERS

(75) Inventors: Kelly Laura Wolff, Appleton, WI (US); Corey T. Cunningham, Larsen, WI (US); Jeffery Richard Seidling, Appleton, WI (US); Thomas O'Lenick, Dacula, GA (US); Anthony G. O'Lenick, Dacula, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 154 days.

This patent is subject to a terminal disclaimer.

(21) Appl. No.: 13/460,320

(22) Filed: Apr. 30, 2012

(65) Prior Publication Data

US 2013/0095163 A1 Apr. 18, 2013

Related U.S. Application Data

(60) Provisional application No. 61/627,478, filed on Oct. 13, 2011.

(51) Int. Cl.
| | |
|---|---|
| *A01N 25/34* | (2006.01) |
| *C11D 3/20* | (2006.01) |
| *A01N 25/30* | (2006.01) |
| *C11D 7/26* | (2006.01) |
| *A01N 25/08* | (2006.01) |
| *C11D 3/00* | (2006.01) |
| *A61Q 17/04* | (2006.01) |
| *C11D 3/48* | (2006.01) |
| *C11D 3/37* | (2006.01) |
| *A61K 8/894* | (2006.01) |
| *A61K 47/34* | (2006.01) |

(52) U.S. Cl.
CPC ............ *C11D 3/0094* (2013.01); *C11D 3/2003* (2013.01); *A01N 25/30* (2013.01); *C11D 7/261* (2013.01); *A01N 25/08* (2013.01); *A61Q 17/04* (2013.01); *C11D 3/2006* (2013.01); *C11D 3/48* (2013.01); *C11D 3/3738* (2013.01); *A61K 8/894* (2013.01); *A61K 47/34* (2013.01)
USPC ........................................................ 424/402

(58) Field of Classification Search
None
See application file for complete search history.

(56) References Cited

U.S. PATENT DOCUMENTS

| | | | |
|---|---|---|---|
| 3,849,241 A | 11/1974 | Butin et al. | |
| 4,100,324 A | 7/1978 | Anderson et al. | |
| 4,440,653 A | 4/1984 | Briscoe et al. | |
| 5,284,703 A | 2/1994 | Everhart et al. | |
| 5,350,624 A | 9/1994 | Georger et al. | |
| 5,629,006 A | 5/1997 | Hoang et al. | |
| 5,635,462 A | 6/1997 | Fendler et al. | |
| 5,843,881 A | 12/1998 | Dubois et al. | |
| 5,951,993 A | 9/1999 | Scholz et al. | |
| 6,117,440 A | 9/2000 | Suh et al. | |
| 6,120,753 A | 9/2000 | Vinski et al. | |
| 6,228,385 B1 | 5/2001 | Shick | |
| 6,258,348 B1 | 7/2001 | Tsivkin | |
| 6,315,991 B1 | 11/2001 | Zofchak et al. | |
| 6,335,000 B1 | 1/2002 | Pratley | |
| 6,432,393 B1 | 8/2002 | Bergmann et al. | |
| 6,723,310 B2 | 4/2004 | Zofchak et al. | |
| 6,946,413 B2 | 9/2005 | Lange et al. | |
| 6,949,249 B2 | 9/2005 | Healy et al. | |
| 7,202,209 B2 | 4/2007 | Chang et al. | |
| 7,381,417 B2 | 6/2008 | Gamez-Garcia | |
| 7,651,990 B2 | 1/2010 | Asmus | |
| 7,670,615 B2 | 3/2010 | Veeger et al. | |
| 7,670,967 B2 | 3/2010 | Runge et al. | |
| 7,842,725 B2 | 11/2010 | Wegner et al. | |
| 7,892,643 B2 | 2/2011 | Kutsovsky | |
| 7,893,285 B2 | 2/2011 | Bettle, III | |
| 8,058,315 B2 | 11/2011 | Wegner et al. | |
| 8,304,375 B1 | 11/2012 | Wolff et al. | |
| 2002/0031486 A1 | 3/2002 | Lunsmann et al. | |
| 2005/0208112 A1* | 9/2005 | Roc et al. ...................... | 424/443 |
| 2005/0222001 A1 | 10/2005 | Baumeister et al. | |
| 2005/0265936 A1 | 12/2005 | Knopf et al. | |
| 2006/0204466 A1 | 9/2006 | Littau et al. | |
| 2006/0281663 A1 | 12/2006 | Asmus | |
| 2007/0027055 A1 | 2/2007 | Koivisto et al. | |
| 2007/0065383 A1 | 3/2007 | De Castro et al. | |
| 2007/0184016 A1 | 8/2007 | Macinga et al. | |
| 2008/0215020 A1 | 9/2008 | Reeves et al. | |
| 2009/0018047 A1 | 1/2009 | Mundschau et al. | |

(Continued)

FOREIGN PATENT DOCUMENTS

| | | |
|---|---|---|
| AU | 2006222502 B2 | 9/2006 |
| EP | 1552807 A1 | 7/2005 |
| EP | 1811013 B1 | 8/2009 |
| EP | 2242475 B1 | 7/2011 |
| WO | 0032575 A1 | 6/2000 |

OTHER PUBLICATIONS

Non-Final Office Action for U.S. Appl. No. 13/460,439 dated Apr. 8, 2013; 12 pages.
International Search Report and Written Opinion for PCT/IB2013/052467, mailed Aug. 9, 2013 (10 pages).
International Search Report and Written Opinion for PCT/IB2013/052466, mailed Aug. 9, 2013 (13 pages).
International Search Report and Written Opinion for PCT/IB2013/052464, mailed Aug. 9, 2013 (11 pages).
http://en.wikipedia.org/wiki/Lipophilicity, 2 pages, 2013.

*Primary Examiner* — Brian Gulledge
(74) *Attorney, Agent, or Firm* — Dority & Manning, P.A.

(57) ABSTRACT

Foaming formulations including silicone polyesters are disclosed. These foaming formulations are useful as cleansing formulations such as used in liquid hand cleansers and wet wipes. The foaming formulations provide improved aesthetic properties and foaming appearance, while maintaining high antimicrobial capacity.

20 Claims, No Drawings

(56) References Cited

U.S. PATENT DOCUMENTS

| | | |
|---|---|---|
| 2009/0018213 A1 | 1/2009 | Snyder et al. |
| 2009/0214628 A1 | 8/2009 | de Rijk |
| 2009/0258812 A1 | 10/2009 | Sengupta et al. |
| 2009/0325837 A1 | 12/2009 | Mundschau et al. |
| 2010/0021464 A1 | 1/2010 | Archambeau et al. |
| 2010/0317595 A1 | 12/2010 | Mullins et al. |
| 2010/0327013 A1 | 12/2010 | Asmus et al. |
| 2011/0104079 A1 | 5/2011 | Synder et al. |

* cited by examiner

FOAMING FORMULATIONS AND CLEANSING PRODUCTS INCLUDING SILICONE POLYESTERS

This application claims priority from U.S. Provisional Application Ser. No. 61/627,478 filed on Oct. 13, 2011, which is hereby incorporated by reference in its entirety.

BACKGROUND OF THE DISCLOSURE

The present disclosure relates generally to a formulation comprising a silicone polyester. The silicone polyester provides the formulation with an improved foaming property. The foaming formulations of the present disclosure are useful as cleansing formulations such as used in liquid hand cleansers and wet wipes.

According to the Center for Disease Control, proper cleansing can be one of the most effective steps taken to prevent the spread of diseases and infections. Specifically, proper bodily cleansing according to various sources requires not only using soap but also washing for a sufficiently long period of time in order to remove dirt and any microorganisms that may be present on the skin. For example, the Center for Disease Control has stated that effective cleansing should last at least 15 seconds.

As many consumers fail to effectively cleanse using soaps, alcohol-based sanitizing solutions and cleansing wipes capable of providing effective antimicrobial sanitation for hand or body cleansing purposes have been developed. Various forms of alcohol-based antimicrobial compositions are known in the art and have been used in the healthcare industry, food service industry, and private sector by individual consumers to provide a convenient means to control and prevent the spread of potentially harmful bacteria and other microorganisms. The alcohol-based antimicrobial compositions and cleansing wipes including the compositions are typically utilized to cleanse the skin by destroying bacteria and other microorganisms present thereon, especially on the hands, arms, and face of the user. Further, cleansing wipes, such as baby wipes, are used to cleanse the sensitive skin of infants.

While providing effective cleansing of the skin, frequent use of alcohol-based antimicrobial compositions and cleansing wipes including the compositions may cause skin irritation and dryness. This can be a problem for health care professionals, child care providers, food service workers and others who use these alcohol-based products to cleanse or sanitize their body multiple times in a day.

To counteract the drying and irritating effects of alcohol gels, foaming alcohol formulations including conventional ethoxylated silicones or conventional fluorinated compounds have been developed. However, these agents may cause the formulations to have poor aesthetics and/or skin feel properties, as well as poor foam stability. In addition, fluorinated compounds impose potential environmental and safety concerns.

Accordingly, there is a need for foaming formulations and cleansing products including the foaming formulations that provide effective skin cleansing and sanitizing effects, while having good foam stability. It would further be advantageous if the foaming formulations and products provided improved aesthetic properties and foaming appearance, while maintaining high antimicrobial capacity.

BRIEF DESCRIPTION OF THE DISCLOSURE

It has now been unexpectedly found that foaming formulations effective for cleansing and sanitizing surfaces can be formed without the use of conventional ethoxylated silicones and conventional fluorinated compounds. Particularly, the foam of a foaming formulation is a two phase system comprised of gas cells, or bubbles, that are surrounded by a thin, continuous liquid film phase. The amount of liquid in the thin film defines the type of foam that is generated. For example, conventional detergent solutions are classified as "wet foams". In a wet foam, the liquid is mainly found in the junctions between gas bubbles, known as "Plateau borders". As the amount of liquid increases relative to the amount of gas bubbles, the thin liquid films surrounding the bubbles and the Plateau borders swell, forcing the bubbles to take a spherical shape. As the swelling increases, the borders lose rigidity and fall apart, causing the foam to degrade into a bubbly liquid that has no overall order or rigidity.

It has now been unexpectedly discovered that specific amphiphilic terpolymers can generate a high quality, stable foam in foaming formulations by preventing swelling of the liquid films against the gas bubbles and Plateau borders. Further, it has been discovered that the polymeric nature of the foaming formulations of the present disclosure provide enhanced skin aesthetics (e.g., substantivity while formulation is in use, reduced tackiness during and after formulation use, soft and conditioned skin feel of formulation, and improved foam appearance).

Accordingly, the present disclosure is directed to a foaming formulation including water and a silicone polyester. The silicone polyester has the following structure:

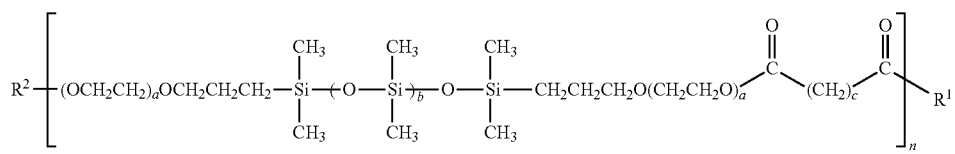

wherein $R^1$ is $-O(CH_2CH_2O)_xCH_3$; $R^2$ is $-C(O)(CH_2)_cC(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25. The foaming formulation is substantially free of $C_1$-$C_6$ alcohols.

The present disclosure is further directed to a cleansing product including a substrate including a foaming formulation. The foaming formulation includes a silicone polyester having the following structure:

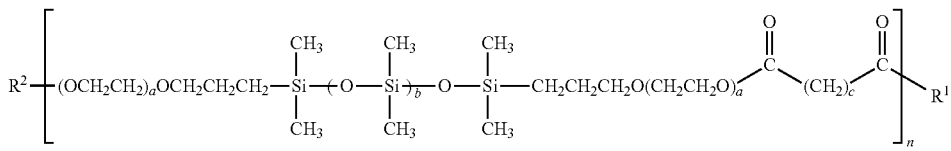

wherein $R^1$ is —O(CH$_2$CH$_2$O)$_x$CH$_3$; $R^2$ is —C(O) (CH$_2$)$_c$C(O)O(CH$_2$CH$_2$O)$_x$CH$_3$; a is an integer ranging from 5 to 20; b is an integer ranging from 10 to 30; c is an integer ranging from 1 to 10; n is an integer ranging from 5 to 15; and x is an integer ranging from 5 to 25. The foaming formulation is substantially free of C$_1$-C$_6$ alcohols. The cleansing products include wipes, such as wet wipes and dry wipes, medical wraps, bandages, and the like.

The present disclosure is further directed to a wet wipe including a substrate including a foaming formulation. The foaming formulation includes water and a silicone polyester. The silicone polyester has the following structure:

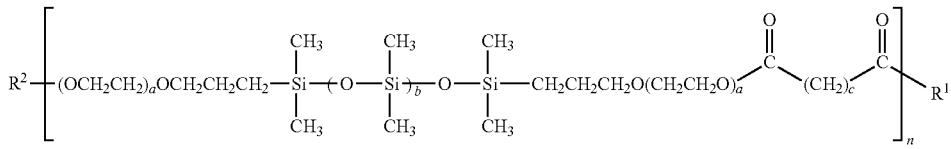

wherein $R^1$ is —O(CH$_2$CH$_2$O)$_x$CH$_3$; $R^2$ is —C(O) (CH$_2$)$_c$C(O)O(CH$_2$CH$_2$O)$_x$CH$_3$; a is an integer ranging from 5 to 20; b is an integer ranging from 10 to 30; c is an integer ranging from 1 to 10; n is an integer ranging from 5 to 15; and x is an integer ranging from 5 to 25. The foaming formulation is substantially free of C$_1$-C$_6$ alcohols.

Other objects and features will be in part apparent and in part pointed out hereinafter.

DEFINITIONS

Within the context of this specification, each term or phrase below will include, but not be limited to, the following meaning or meanings:

(a) "Liquid formulation" refers to both liquid and gel formulations. Non-limiting examples of liquid foaming formulations of the present disclosure include wet wipe solutions, body cleansers, hair shampoos, and the like.

(b) "Bonded" refers to the joining, adhering, connecting, attaching, or the like, of two elements. Two elements will be considered to be bonded together when they are bonded directly to one another or indirectly to one another, such as when each is directly bonded to intermediate elements.

(c) "Film" refers to a thermoplastic film made using a film extrusion and/or forming process, such as a cast film or blown film extrusion process. The term includes apertured films, slit films, and other porous films which constitute liquid transfer films, as well as films which do not transfer liquid.

(d) "Layer" when used in the singular can have the dual meaning of a single element or a plurality of elements.

(e) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. (Nov. 19, 1974). Meltblown fibers are microfibers which may be continuous or discontinuous, are generally smaller than about 0.6 denier, and are generally self bonding when deposited onto a collecting surface. Meltblown fibers used in the present disclosure are preferably substantially continuous in length.

(f) "Nonwoven" refers to materials and webs of material which are formed without the aid of a textile weaving or knitting process.

(g) "Polymeric" includes, but is not limited to, homopolymers, copolymers, such as for example, block, graft, random and alternating copolymers, terpolymers, etc. and blends and modifications thereof. Furthermore, unless otherwise specifically limited, the term "polymeric" shall include all possible geometrical configurations of the material. These configurations include, but are not limited to, isotactic, syndiotactic and atactic symmetries.

(h) "Thermoplastic" describes a material that softens when exposed to heat and which substantially returns to a nonsoftened condition when cooled to room temperature.

DETAILED DESCRIPTION OF THE DISCLOSURE

The present disclosure is directed to a foaming formulation comprising a silicone polyester. The foaming formulation provides effective cleansing and/or sanitizing of an animate or inanimate surface without the use of C1-C6 alcohols. Further, the foaming formulation has an improved foaming effect, while further having improved aesthetics and skin-feel. Surprisingly, the formulation has improved foam stability as compared to foaming formulations including conventional ethoxylated silicones and conventional fluorinated compounds.

Typically, the foaming formulations of the present disclosure include a silicone polyester. The silicone polyester includes three active groups (i.e., an amphiphilic terpolymer) having differing solubilities in aqueous conditions. These different solubilities allow for the enhanced stabilization of foam in the formulation. Further, the polymeric nature provides enhanced skin aesthetics and skin feel.

The silicone polyesters used in the foaming formulations of the present disclosure are prepared by an esterification reaction, in which linear dicarboxylic acid reacts with poly (ethylene glycol) monomethyl ether and dimethicone copolyols (LDMC). The resulting silicone polyesters conform to the following structure:

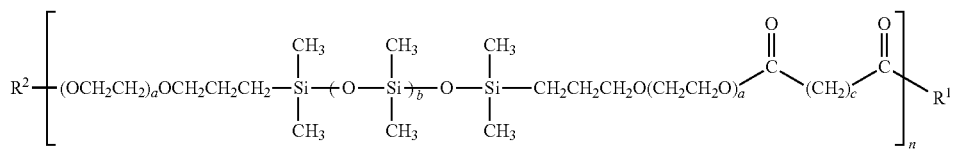

wherein $R^1$ is $-O(CH_2CH_2O)_xCH_3$; $R^2$ is $-C(O)(CH_2)_cC(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25. Commercially available silicone polyesters for use in the foaming formulations of the present disclosure are available from Siltech Corporation (Ontario, Canada).

Dicarboxylic acid compounds for use in the esterification reaction are commercially available from a variety of sources (e.g., Cognis, Cincinnati, Ohio) and conform to the following structure:

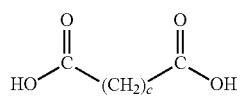

wherein c is an integer ranging from 1 to 10.

Suitably, $C_1$-$C_{10}$ saturated dicarboxylic acids for use in the esterification reaction are as follows:

| Common Name | c | Molecular Weight |
|---|---|---|
| Malonic | 1 | 104 |
| Succinic | 2 | 118 |
| Glutaric | 3 | 132 |
| Adipic | 4 | 146 |

-continued

| Common Name | c | Molecular Weight |
|---|---|---|
| Pimelic | 5 | 160 |
| Subric | 6 | 174 |
| Azelaic | 7 | 188 |
| Sebacic | 8 | 202 |
| Undecanedioic | 9 | 216 |
| Dodecanedioic | 10 | 230 |

Poly(ethylene glycol) monomethyl ethers for use in the esterification reaction are commercially available from a variety of sources, such as FCI Technology (Gastonia, N.C.), and conform to the following structure:

$$CH_3-O-(CH_2CH_2O)_x-H$$

wherein x is an integer from 5 to 25.

Suitable examples of poly(ethylene glycol) monomethyl ethers for use in the esterification reaction include the following:

| x | Molecular Weight |
|---|---|
| 5 | 237 |
| 8 | 367 |
| 15 | 676 |
| 23 | 1027 |
| 25 | 1116 |

LDMC compounds for use in the esterification reaction are commercially available from Siltech LLC (Lawrenceville, Ga.), and conform to the following structure:

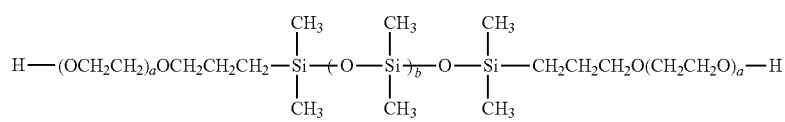

wherein a is an integer ranging from 5 to 20 and b is an integer ranging from 10 to 30.

Suitably, LDMC is selected from the following compounds:

| a  | b  | Molecular Weight |
|----|----|------------------|
| 5  | 10 | 1137             |
| 10 | 10 | 1357             |
| 20 | 10 | 1797             |
| 5  | 20 | 1876             |
| 10 | 20 | 2096             |
| 20 | 20 | 2536             |
| 5  | 30 | 2616             |
| 10 | 30 | 2836             |
| 20 | 30 | 3276             |

The values above were determined by $^{13}$C NMR, $^{29}$Si NMR and Gel Permeation Chromatography (GPC).

The foaming formulations include the silicone polyesters in amounts of from about 0.01% by weight to about 5.0% by weight, including from about 0.1% by weight to about 4.0% by weight, and including from about 0.25% by weight to about 2.5% by weight. In one suitable embodiment, the foaming formulation includes about 2.0% by weight silicone polyester.

In particularly suitable embodiments, the foaming formulation is in the form of a liquid formulation including from about 30% by weight to about 99% by weight water, including from about 50% by weight to about 95% by weight water, including from about 60% by weight to about 93% by weight water, and including from about 70% to about 90% by weight water. In one embodiment, the liquid foaming formulation is used as the wetting solution of a wet wipe and includes from about 70% by weight to about 99% by weight water.

In some embodiments, the foaming formulation may also include various optional agents to modify the physical, chemical, hedonic or processing characteristics of the formulations or serve as beneficial agents when used for a targeted purpose or in a targeted user population. The optional agents include, for example, emollients, humectants, moisturizers, botanicals, foam stabilizers, vitamins, disinfectants, non-aqueous solvents, preservatives, pH modifiers, sequestrants, antimicrobials, antioxidants, anti-reddening agents, astringents, deodorants, external analgesics, film formers, fragrances, hydrotropes, opacifiers, skin conditioning agents, skin exfoliating agents, skin protectants, sunscreens, thickeners, and the like.

Generally, emollients lubricate, soothe, and soften the skin surface. Exemplary emollients include oily or waxy ingredients such as esters, ethers, fatty alcohols, hydrocarbons, silicones, ethoxylated lanolin, and the like, and combinations thereof.

Particular moisturizers could include, but are not to be limited to, PEG-7 glyceryl cocoate, isopropyl palmitate, $C_{12}$-$C_{15}$ alkyl benzoate, natural oils such as jojoba oil, synthetic oils such as mineral oil, silicones such as dimethicone, greater than or equal to $C_8$ fatty alcohols (e.g., cetyl alcohol), fatty acids such as stearic acid, waxes such as beeswax, and the like. One skilled in the art will recognize that this list is not all inclusive and could include any other suitable materials commonly known in the art or referenced in the Personal Care Products Council (PCPC) Compilation of Ingredients Used in Cosmetics in the United States (CIUCUS).

Humectants are hydroscopic agents that are widely used as moisturizers. Their function is to prevent the loss of moisture from the skin and to attract moisture from the environment. Common humectants include, for example, glycerin, propylene glycol, butylene glycol, betaine, sodium hyaluronate, sorbitol, urea, hydroxyethyl urea, and the like, and combinations thereof.

The formulations may further include abrasives, such as sodium carbonate, calcium carbonate, pumice, polyethylene, and the like. Furthermore, the formulation may include builders, such as tripolyphosphate, acrylic homo and copolymers, and the like.

Exemplary disinfectants for use in the foaming formulations include triclosan, quaternary ammonium compounds, phenolics, and essential oils having antimicrobial action (e.g., thyme, eucalyptus, neem), and combinations thereof.

Another additive for use in the formulation may be one or more non-aqueous solvents. Although not required, non-aqueous solvents may aid in dissolving certain components (e.g., preservatives, anti-microbial agent, etc.). Examples of some suitable non-aqueous solvents include, but are not limited to, glycerin, glycols, such as propylene glycol, butylene glycol, triethylene glycol, hexylene glycol, polyethylene glycols, ethoxydiglycol, and dipropyleneglycol, triglycerides, ethyl acetate, acetone, triacetin, and combinations thereof.

Preservatives for increasing the shelf life of the formulations may also be used. Exemplary suitable preservatives include, but are not limited to, Kathon CG, which is a mixture of methylchloroisothiazolinone and methylisothiazolinone, available from Dow Chemical Company, Midland, Mich.; Mackstat H 66, available from Rhodia, member of the Solvay Group, Bristol, Pa.; DMDM hydantoin (e.g., Glydant Plus, Lonza, Inc., Switzerland); tetrasodium EDTA; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Ashland Inc., Ashland, Ky., such as "Germall 115" (amidazolidinyl urea), "Germall II" (diazolidinyl urea), and "Germall Plus" (diazolidinyl urea and iodopropynyl butylcarbonate).

Suitable skin conditioning agents for use in the foaming formulations include quaternium and polyquaternium ingredients. Particularly suitable quaternium ingredients include behentrimonium chloride, behentrimonium methosulfate, cetrimonium chloride, cocotrimonium chloride, quaternium-79 hydrolyzed collagen, quaternium-80, quaternium-88, quaternium-95, and $C_{10}$-$C_{40}$ isoalkylamidopropylethyldimonium ethosulfate. Particularly suitable polyquaternium ingredients include polyquaternium-2, polyquaternium-7, polyquaternium-10, polyquaternium-68, polyquaterium-78, polyquaternium-82, and polymethylacrylamidopropyltrimonium chloride.

In general, the pH of the foaming formulations may be controlled to be within any desired range, depending on the targeted use. By way of example, for bodily cleansing, it is typically desirable to have a foaming formulation with a neutral pH. If necessary, various pH modifiers may be utilized in the foaming formulation to achieve the desired pH level. For instance, some examples of basic pH modifiers that may be used in the formulations of the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the formulations of the present disclosure include, but are not limited to, mineral acids; carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include carrageenic acid, humic acid, fulvic acid, and alginic acid.

In one embodiment, the foaming formulation may additionally include one or more sequestrants. A sequestrant is a substance whose molecules can form one or more bonds with a metal ion. In particular, water that may be contained in the foaming formulation often contains metal ions, such as calcium ions, that might react with anionic components (e.g., acids) present within the foaming formulation. For example, in one embodiment, an anionic component that remains substantially unreacted with metal ions can better function as a cleansing agent. Some examples of sequestrants that may be used in the foaming formulations of the present disclosure include, but are not limited to, ethylenediamines, ethylenediaminetetraacetic acids (EDTA) acid and/or salts thereof, citric acids and/or salts thereof, glucuronic acids and/or salts thereof, iminodisuccinic acid and/or salts thereof, polyphosphates, organophosphates, dimercaprols, and the like.

In order to better enhance the antimicrobial efficacy of the foaming formulation, antimicrobial agents (e.g., chlorohexidine digluconate, polyhexamethylene biguanide (PHMB), benzalkonium chloride, benzethonium chloride, cetyl pyridinium chloride) can also be included in the formulation.

Still other optional agents include: antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); botanicals (e.g., Actiphyte of Aloe Vera 10 Fold GL, Actiphyte of Cucumber GL, Actiphyte of Japanese Green Tea GL, all from The Lubrizol Corporation, Wickliffe, Ohio); foam stabilizers (e.g. Polyox WSR 205 from Dow Chemical Company, Midland, Mich.); vitamins (e.g., tocopheryl acetate, retinyl palmitate, panthenol); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some antimicrobial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens and thickeners (to increase the viscosity of the formulation).

The amounts of the optional components will depend on the formulation to be prepared and the amounts of the other components in the foaming formulation.

The foaming formulations of the present disclosure are substantially free of $C_1$-$C_6$ alcohols. In this context, and unless otherwise specified, the term "substantially free" means that the foaming formulations contain less than a functional amount of $C_1$-$C_6$ alcohols, typically less than 0.1%, including less than 0.05%, including less than 0.001%, and also including zero percent, by weight of $C_1$-$C_6$ alcohols.

In some embodiments, the foaming formulations of the present disclosure are additionally substantially free of agents that are capable of forming micelles, and particularly, substantially free of conventional ethoxylated silicones (e.g., Bis-PEG(10-20) dimethicones), 3-(3-hydroxypropyl)heptamethyl-trisiloxane, polysiloxane betaine, and polyalkylene-modified siloxane block copolymers. In this context, and unless otherwise specified, the term "substantially free" means that the foaming formulations contain less than a functional amount of micelle-forming agents, typically less than 1.0%, including less than 0.5%, including less than 0.1%, and also including zero percent, by weight of micelle-forming agents.

Conventional ethoxylated silicones (e.g., Bis-PEG(10-20) dimethicones), 3-(3-hydroxypropyl)heptamethyl-trisiloxane, polysiloxane betaine, and polyalkylene-modified siloxane block copolymers, used to create foam in conventional foaming formulations may cause the formulations to have poor aesthetics and/or skin feel properties such as a sticky, soapy, and/or tacky skin feel. Further, these conventional foaming formulations have poor foam stability (e.g., bubbly liquid having no overall order, no rigidity, etc.). Accordingly, by avoiding the use of these agents in the foaming formulations of the present disclosure, the foaming formulations provide improved cleansing and/or sanitizing to the skin of the user, and further have improved stability.

Methods of Preparing the Formulations

The foaming formulations are generally prepared by mixing all components together to form a homogeneous solution. Typically, the foaming formulation is prepared by mixing the silicone polyester, typically with water, and with any further optional agents minimizing aeration. In one embodiment, the silicone polyester is mixed with water and any additional components at room temperature.

When used as a liquid formulation, any solid components are first completely dissolved in water or other solvents before mixing with other components. The liquid foaming formulations can be dispensed from a pump or aerosol as generally available in the art.

Cleansing Products Including the Foaming Formulation

In some embodiments, the foaming formulations may be applied to one or more substrates to provide for a cleansing product. For example, the foaming formulation is suitable for use in a number of cleansing products, including personal care products such as wipes and wraps such as medical wraps and bandages, and the like. Although described primarily herein in relation to the wipes, it will be recognized by one skilled in the art that the foaming formulations described herein could be incorporated into any one or more of the other products listed above.

Generally, the wipes of the present disclosure including the foaming formulation can be wet wipes or dry wipes. As used herein, the term "wet wipe" means a wipe that includes greater than 700 (by weight substrate) moisture content. As used herein, the term "dry wipe" means a wipe that includes less than 100 (by weight substrate) moisture content. When a dry wipe is to be used for cleansing, the wipe is typically wetted with an aqueous solution prior to using the wipe to solubilize the silicone polyester to provide for the foaming effects. Specifically, suitable wipes for use in the present disclosure can include wet wipes, hand wipes, face wipes, cosmetic wipes, household wipes, industrial wipes, and the like. Particularly preferred wipes are wet wipes, such as baby wipes and perineal wipes.

Materials suitable for the substrate of the wipes are well know to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter and desirably from about 40 grams per square meter to about 90 grams per square meter.

In one particular embodiment, the wipes of the present disclosure comprise a coform basesheet of polymer fibers and absorbent fibers having a basis weight of from about 60 to about 80 grams per square meter and desirably about 75 grams per square meter. Such coform basesheets are manufactured generally as described in U.S. Pat. No. 4,100,324, issued to Anderson, et al. (Jul. 11, 1978); U.S. Pat. No. 5,284, 703, issued to Everhart, et al. (Feb. 8, 1994); and U.S. Pat. No. 5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Washington); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

In an alternative embodiment, the wipes of the present disclosure can comprise a composite which includes multiple layers of materials. For example, the wipes may include a three layer composite which includes an elastomeric film or meltblown layer between two coform layers as described above. In such a configuration, the coform layers may define a basis weight of from about 15 grams per square meter to about 30 grams per square meter and the elastomeric layer may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

In some embodiments, the substrates used in the cleansing products of the present disclosure, and particularly in the wipes, include polymers and polymer formulations that are treated with salt-sensitive triggerable binder formulations so as to be used as flushable cleansing and personal care products. These triggerable binder formulations can be used in wet wipes for personal use, such as cleaning skin or mucosa, make-up removal, medical care, and the like.

Exemplary triggerable binder formulations include acrylamide and vinylamide/amine polymers or polymer formulations as described in U.S. Pat. No. 7,670,967 (Runge et al., Mar. 2, 2010). The triggerable binder formulations may be applied to any of the above-described fibrous substrates.

The triggerable binder formulation may be applied to the fibrous substrate by any process of application as known in the art. Suitable processes for applying the triggerable binder formulation include, but are not limited to, printing, spraying, electrostatic spraying, coating, flooded nips, metered press rolls, impregnating or by any other technique. The amount of the triggerable binder formulation may be metered and distributed uniformly within the fibrous substrate or may be non-uniformly distributed within the fibrous substrate. The triggerable binder formulation may be distributed throughout the entire fibrous substrate or it may be distributed within a multiplicity of small closely spaced areas. Alternatively, the formulation may be applied in various patterns, such as in well defined straight lines, wavy lines, or sloppy patterns. The triggerable binder formulation may be applied to the fibers prior to incorporation of the fibers into a fibrous substrate.

The solution of the triggerable binder formulation may contain up to about 50 percent by weight of triggerable binder formulation solids. More specifically, the solution of the triggerable binder formulation may contain from about 2 to about 20 percent by weight of triggerable binder formulation solids, more specifically about 5 to about 10 percent by weight of triggerable binder formulation solids.

Once the triggerable binder formulation is applied to the fibrous substrate, the fibrous substrate may be dried by any conventional means. Once dry, the coherent fibrous substrate exhibits improved in-use tensile strength when compared to the in-use tensile strength of the untreated wet-laid or air-laid fibrous substrates, and yet has the ability to rapidly "fall apart", or disintegrate when placed in soft or hard water having a divalent ion concentration of about 500 ppm or greater of $Ca^{2+}$ and/or $Mg^{2+}$, and agitated. For example, the dry tensile strength of the triggerable binder formulation treated fibrous substrate may be increased by at least about 25% as compared to the dry tensile strength of the untreated fibrous substrate. More particularly, the dry tensile strength of the triggerable binder formulation treated fibrous substrate may be increase by at least about 100% as compared to the dry tensile strength of the untreated fibrous substrate. Even more particularly, the dry tensile strength of the fibrous substrate treated with the triggerable binder formulation may be increased by at least about 500% as compared to the dry tensile strength of the untreated fibrous substrate.

Typically, the wipes of the present disclosure include the foaming formulation in an add-on amount of from about 150% by weight to about 600% by weight dry basesheet, including from about 175% by weight to about 450% by weight dry basesheet, and including from about 200% by weight to about 400% by weight dry basesheet.

Methods of Use

The foaming formulations and cleansing products including the formulations of the present disclosure can be used to provide effective cleansing and/or sanitizing of animate and inanimate surfaces. In one embodiment, the foaming formulations may be used to clean and/or sanitize a user's body. These foaming formulations are capable of being topically applied to the skin of a user to kill and/or inhibit the growth of bacteria and other microorganisms on the skin, particularly, on the hands, arms, and face of a user.

Moreover, the foaming formulations provide a cleansing effect without the use of irritating components such as $C_1$-$C_6$ alcohols. Accordingly, the user can effectively cleanse the body without irritation and skin damage.

The foaming formulations have improved stability such that the foaming formulations provide a cleansing effect for a sufficiently long period of time in order to effectively remove dirt and microorganisms. The foaming formulations have improved aesthetics (e.g., soft feel, improved foam appearance (e.g., even dispersion of foam from a dispensing device, smaller, more densely packed gas bubbles having uniform size and density, gas bubbles that do not degrade or convert quickly to a bubbly liquid)) and skin-feel.

In other embodiments, the foaming formulations can be applied to substrates to provide for effective cleansing and/or sanitizing of animate and inanimate surfaces. The foaming formulations can be applied to the substrates using any means known in the formulation application art, including, for example, coating, spraying, dripping, dipping, and combinations thereof. In one particularly desirable embodiment, the formulation is applied to the substrate using slot die coating. Using the slot die coating process has been found to provide good add-on control.

The formulation can be applied to one or more surfaces of the substrate, including an outer surface, an inner surface, ends or edges of the substrate, and combinations thereof.

Having described the disclosure in detail, it will be apparent that modifications and variations are possible without departing from the scope of the disclosure defined in the appended claims.

EXAMPLES

The following non-limiting Examples are provided to further illustrate the present disclosure.

Example 1

In this Example, a suitable foaming formulation of the present disclosure was prepared for use as a liquid hand cleanser. The components of the formulation are shown in the table below.

| Component | INCI Name | Wt % |
|---|---|---|
| Water | | q.s. to 100 |
| Carbopol Aqua SF-1 (The Lubrizol Corporation, Wickliffe, Ohio) | Acrylate Copolymer | 4.00 |
| Silicone Polyester (Siltech Corporation, Ontario, Canada) | Methyl PEG-8 Bis-PEG-10 Dimethicone Succinate Copolymer | 2.00 |
| Amphosol CA (Stepan Company, Northfield, Illinois) | Cocamidopropyl Betaine | 5.00 |
| Plantaren 2000N UP (Cognis Corporation, Cincinnati, Ohio) | Decyl Glucoside | 5.00 |
| Lamesoft PO 65 (Cognis Corporation, Cincinnati, Ohio) | Coco-Glucoside, Glyceryl Oleate | 1.50 |
| Glycerin | Glycerin | 1.50 |
| Fragrance | Fragrance | 0.10 |
| Dye | Dye | 0.02 |
| Glydant | DMDM Hydantoin | 0.50 |
| Citric Acid | Citric Acid | to pH 5.5 |

To prepare the foaming formulation, water was first added to a vessel. While stirring the water, the silicone polyester, betaine, glucosides, glycerin, fragrance, dye, and antimicrobial agent were added to the solution. Finally, citric acid was added to reach a final pH of approximately 5.5, and the mixture was mixed to homogeneity at room temperature.

Example 2

In this Example, a suitable foaming formulation of the present disclosure was prepared using the method of Example 1 for use as a foaming hand wash. The components of the formulation are shown in the table below.

| Component | INCI Name | Wt % |
|---|---|---|
| Water | | q.s. to 100 |
| Silicone Polyester (Siltech Corporation, Ontario, Canada) | Methyl PEG-8 Bis-PEG-10 Dimethicone Succinate Copolymer | 2.00 |
| Amphosol CA (Stepan Company, Northfield, Illinois) | Cocamidopropyl Betaine | 5.00 |
| Fragrance | Fragrance | 0.10 |
| Dye | Dye | 0.02 |
| Glydant | DMDM Hydantoin | 0.50 |
| Citric Acid | Citric Acid | to pH 5.5 |

Example 3

In this Example, a suitable foaming formulation of the present disclosure was prepared for use as a non-alcohol hand sanitizer. The components of the formulation are shown in the table below.

| Component | INCI Name | Wt % |
|---|---|---|
| Water | | q.s. to 100 |
| Silicone Polyester (Siltech | Methyl PEG-8 Bis-PEG-10 Dimethicone Succinate Copolymer | 2.00 |

-continued

| Component | INCI Name | Wt % |
|---|---|---|
| Corporation, Ontario, Canada) | | |
| Nobac (Mason Chemical Company, Arlington Heights, Illinois) | Benzalkonium Chloride | 0.20 |
| Baypure CX-100 (Bayer Chemical AG, Germany) | Tetrasodium Iminodisuccinic Acid | 0.23 |
| Citric Acid | Citric Acid | to pH 5.5 |

To prepare the formulation, water was first added to a vessel. While stirring the water, the silicone polyester, benzalkonium chloride, and tetrasodium iminodosuccinic acid were added to the solution. Finally, citric acid was added to reach a final pH of approximately 5.5, and the mixture was mixed to homogeneity at room temperature.

Example 4

In this Example, a suitable foaming formulation of the present disclosure was prepared for use as a leave-on moisturizing foam. The components of the formulation are shown in the table below.

| Component | INCI Name | Wt % |
|---|---|---|
| Water | | q.s. to 100 |
| Silicone Polyester (Siltech Corporation, Ontario, Canada) | Methyl PEG-8 Bis-PEG-10 Dimethicone Succinate Copolymer | 2.00 |
| Betafin BP-20 (Danisco A/S, Denmark) | Betaine | 2.00 |
| Glycerin | Glycerin | 2.00 |
| Citric Acid | Citric Acid | to pH 5.5 |

To prepare the foaming formulation, water was first added to a vessel. While stirring the water, the silicone polyester, betaine, and glycerin were added to the solution. Finally, citric acid was added to reach a final pH of approximately 5.5, and the mixture was mixed to homogeneity at room temperature.

Example 5

In this Example, a suitable foaming formulation of the present disclosure was prepared and applied to a substrate to be used as a baby wipe. The components of the formulation are shown in the table below.

| Component | INCI Name | Wt % |
|---|---|---|
| Water | | q.s. to 100 |
| Silicone Polyester (Siltech Corporation, Ontario, Canada) | Methyl PEG-8 Bis-PEG-10 Dimethicone Succinate Copolymer | 0.50 |
| Glycerin | Glycerin | 0.50 |
| Tween 20 (Sigma-Aldrich, St. Louis, Missouri) | Polysorbate-20 | 0.10 |

-continued

| Component | INCI Name | Wt % |
|---|---|---|
| Purox S (Kalama Chemical, Kalama, Washington) | Sodium Benzoate | 0.45 |
| Neolone 950 (The Dow Chemical Company, Midland, Michigan) | Methylisothiazolinone | 0.09 |
| Fragrance | Fragrance | 0.05 |
| Baypure CX-100 (Bayer Chemical AG, Germany) | Tetrasodium Iminodisuccinic Acid | 0.20 |
| Malic Acid | Malic Acid | to pH 5.5 |

To prepare the foaming formulation, water was first added to a vessel. While stirring the water, the silicone polyester, glycerin, Polysorbate-20, sodium benzoate, methylisothiazolinone, fragrance, and tetrasodium iminodisuccinic acid were added to the solution. Finally, malic acid was added to reach a final pH of approximately 5.5, and the mixture was mixed to homogeneity at room temperature.

Once prepared, the foaming formulation was applied to a coform basesheet at an add-on amount of 330% by weight dry coform basesheet.

Example 6

In this Example, a suitable foaming formulation of the present disclosure was prepared and applied to a substrate to be used as a perineal wipe. The components of the formulation are shown in the table below.

| Component | INCI Name | Wt % |
|---|---|---|
| Water | | q.s. to 100 |
| Silicone Polyester (Siltech Corporation, Ontario, Canada) | Methyl PEG-8 Bis-PEG-10 Dimethicone Succinate Copolymer | 0.50 |
| Culinox 999 (Morton Salt, Chicago, Illinois) | Sodium Chloride | 2.00 |
| Silfactant D-20-6 | Polysorbate-20 | 0.20 |
| Purox S (Kalama Chemical, Kalama, Washington) | Sodium Benzoate | 0.45 |
| Neolone 950 (The Dow Chemical Company, Midland, Michigan) | Methylisothiazolinone | 0.09 |
| Fragrance | Fragrance | 0.05 |
| Baypure CX-100 (Bayer Chemical AG, Germany) | Tetrasodium Iminodisuccinic Acid | 0.23 |
| Citric Acid | Citric Acid | to pH 5.5 |

To prepare the formulation, water was first added to a vessel. While stirring the water, the silicone polyester, sodium chloride, Polysorbate-20, sodium benzoate, methylisothiazolinone, fragrance, and tetrasodium iminodisuccinic acid were added to the solution. Finally, citric acid was added to reach a final pH of approximately 5.5, and the mixture was mixed to homogeneity at room temperature.

Once prepared, the formulation was applied to a dispersible airlaid basesheet at an add-on amount of 250% by weight dry dispersible airlaid basesheet.

When introducing elements of the present disclosure or the preferred embodiment(s) thereof, the articles "a", "an", "the"

What is claimed is:

1. A foaming formulation comprising water and a silicone polyester, wherein the silicone polyester comprises the following structure:

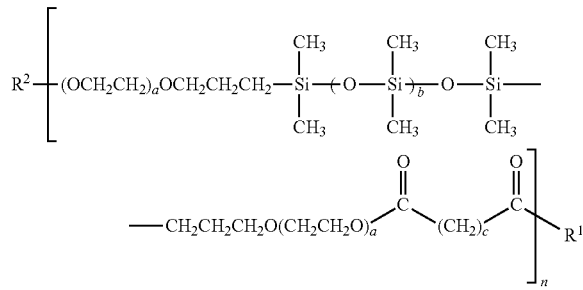

wherein $R^1$ is $—O(CH_2CH_2O)_xCH_3$; $R^2$ is $—C(O)(CH_2)_c$ $C(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25, and wherein the foaming formulation is substantially free of $C_1$-$C_6$ alcohols.

2. The foaming formulation of claim 1 comprising from about 30% by weight to about 99% by weight water and from about 0.01% by weight to about 5.0% by weight silicone polyester.

3. The foaming formulation of claim 1 comprising from about 0.1% by weight to about 4.0% by weight silicone polyester.

4. The foaming formulation of claim 1 comprising from about 0.25% by weight to about 2.5% by weight silicone polyester.

5. The foaming formulation of claim 1 further comprising at least one agent selected from the group consisting of emollients, humectants, moisturizers, botanicals, foam stabilizers, vitamins, disinfectants, abrasives, non-aqueous solvents, preservatives, pH modifiers, sequestrants, antimicrobials, antioxidants, anti-reddening agents, astringents, deodorants, external analgesics, film formers, fragrances, hydrotropes, opacifiers, skin conditioning agents, skin exfoliating agents, skin protectants, sunscreens, and thickeners.

6. A cleansing product comprising a substrate comprising a foaming formulation, the foaming formulation comprising a silicone polyester comprising the following structure:

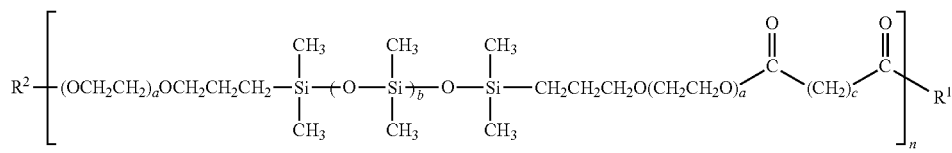

wherein $R^1$ is $—O(CH_2CH_2O)_xCH_3$; $R^2$ is $—C(O)(CH_2)_c$ $C(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25, wherein the foaming formulation is substantially free of $C_1$-$C_6$ alcohols.

7. The cleansing product of claim 6 wherein the substrate is a nonwoven substrate.

8. The cleansing product of claim 6 wherein the substrate is a woven substrate.

9. The cleansing product of claim 6 wherein the product is selected from the group consisting of wipes, medical wraps, and bandages.

10. The cleansing product of claim 6 wherein the foaming formulation comprises from about 0.01% by weight to about 5.0% by weight silicone polyester.

11. The cleansing product of claim 6 wherein the foaming formulation comprises from about 0.1% by weight to about 4.0% by weight silicone polyester.

12. The cleansing product of claim 6 wherein the foaming formulation comprises from about 0.25% by weight to about 2.5% by weight silicone polyester.

13. The cleansing product of claim 6 wherein the foaming formulation further comprises at least one agent selected from the group consisting of emollients, humectants, moisturizers, botanicals, foam stabilizers, vitamins, disinfectants, abrasives, non-aqueous solvents, preservatives, pH modifiers, sequestrants, antimicrobials, antioxidants, anti-reddening agents, astringents, deodorants, external analgesics, film formers, fragrances, hydrotropes, opacifiers, skin conditioning agents, skin exfoliating agents, skin protectants, sunscreens, and thickeners.

14. A wet wipe comprising a substrate comprising a foaming formulation, the foaming formulation comprising water and a silicone polyester, wherein the silicone polyester comprises the following structure:

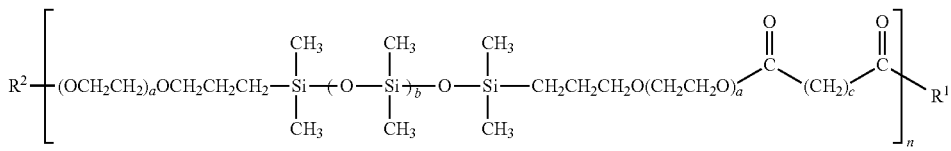

wherein $R^1$ is —$O(CH_2CH_2O)_xCH_3$; $R^2$ is —$C(O)(CH_2)_c C(O)O(CH_2CH_2O)_xCH_3$; a is an integer ranging from 5 to 20; b is an integer ranging from 10 to 30; c is an integer ranging from 1 to 10; n is an integer ranging from 5 to 15; and x is an integer ranging from 5 to 25, and wherein the foaming formulation is substantially free of $C_1$-$C_6$ alcohols.

15. The wet wipe of claim 14 wherein the wet wipe comprises from about 150% to about 600% by weight dry substrate of the foaming formulation.

16. The wet wipe of claim 14 wherein the wet wipe is selected from the group consisting of baby wipes, perineal wipes, hand wipes, face wipes, cosmetic wipes, household wipes, and industrial wipes.

17. The wet wipe of claim 14 wherein the foaming formulation comprises from about 70% by weight to about 99% by weight water and from about 0.01% by weight to about 5.0% by weight silicone polyester.

18. The wet wipe of claim 14 wherein the foaming formulation comprises from about 0.1% by weight to about 4.0% by weight silicone polyester.

19. The wet wipe of claim 14 wherein the foaming formulation comprises from about 0.25% by weight to about 2.5% by weight silicone polyester.

20. The wet wipe of claim 14 wherein the foaming formulation further comprises at least one agent selected from the group consisting of emollients, humectants, moisturizers, botanicals, foam stabilizers, vitamins, disinfectants, abrasives, non-aqueous solvents, preservatives, pH modifiers, sequestrants, antimicrobials, antioxidants, anti-reddening agents, astringents, deodorants, external analgesics, film formers, fragrances, hydrotropes, opacifiers, skin conditioning agents, skin exfoliating agents, skin protectants, sunscreens, and thickeners.

* * * * *